United States Patent [19]

Ullman et al.

[11] Patent Number: 4,597,776
[45] Date of Patent: Jul. 1, 1986

[54] HYDROPYROLYSIS PROCESS

[75] Inventors: Alan Z. Ullman, Northridge; Jacob Silverman, Woodland Hills; Joseph Friedman, Huntington Beach, all of Calif.

[73] Assignee: Rockwell International Corporation, El Segundo, Calif.

[21] Appl. No.: 693,319

[22] Filed: Jan. 22, 1985

Related U.S. Application Data

[63] Continuation of Ser. No. 432,231, Oct. 1, 1982, abandoned.

[51] Int. Cl.$^4$ .................................................. C10J 3/46
[52] U.S. Cl. .................................... 48/197 R; 48/206; 48/210; 201/29; 201/38; 423/655; 423/659; 585/733; 585/943
[58] Field of Search ................... 48/197 R, 202, 206, 48/209, 210, 213; 252/373; 585/733, 943; 423/648 R, 655, 659; 201/28, 29, 38

[56] References Cited

U.S. PATENT DOCUMENTS

| | | | |
|---|---|---|---|
| 2,840,462 | 6/1958 | Gorin | 585/733 |
| 3,698,882 | 10/1972 | Garret et al. | 48/210 |
| 3,847,567 | 11/1974 | Kalina et al. | 48/202 |
| 3,874,116 | 4/1975 | White | 48/209 |
| 3,993,457 | 11/1976 | Cahn et al. | 48/197 R |
| 4,121,912 | 10/1978 | Barber et al. | 48/197 R |
| 4,162,959 | 7/1979 | Duraiswamy | 208/8 R |
| 4,183,733 | 1/1980 | Jager | 48/77 |
| 4,217,201 | 8/1980 | Chervenak | 208/8 R |
| 4,229,185 | 10/1980 | Sass | 48/197 R |
| 4,312,638 | 1/1982 | Koump | 48/197 R |
| 4,322,222 | 3/1982 | Sass | 48/197 R |

OTHER PUBLICATIONS

Gallagher, Jr., J. E., and Marshall, H. A., "Production of SNG from Illinois Coal via Catalytic Gasification", *AIChE Symposium on Reactor Engineering in Processing Solid Fossil Fuels,* Nov. 1978.

*Primary Examiner*—Barry S. Richman
*Assistant Examiner*—Joye L. Woodard
*Attorney, Agent, or Firm*—H. Fredrick Hamann; Harry B. Field; Clark E. DeLarvin

[57] ABSTRACT

An improved process for producing a methane-enriched gas wherein a hydrogen-deficient carbonaceous material is treated with a hydrogen-containing pyrolysis gas at an elevated temperature and pressure to produce a product gas mixture including methane, carbon monoxide and hydrogen. The improvement comprises passing the product gas mixture sequentially through a water-gas shift reaction zone and a gas separation zone to provide separate gas streams of methane and of a recycle gas comprising hydrogen, carbon monoxide and methane for recycle to the process. A controlled amount of steam also is provided which when combined with the recycle gas provides a pyrolysis gas for treatment of additional hydrogen-deficient carbonaceous material. The amount of steam used and the conditions within the water-gas shift reaction zone and gas separation zone are controlled to obtain a steady-state composition of pyrolysis gas which will comprise hydrogen as the principal constituent and a minor amount of carbon monoxide, steam and methane so that no external source of hydrogen is needed to supply the hydrogen requirements of the process. In accordance with a particularly preferred embodiment, conditions are controlled such that there also is produced a significant quantity of benzene as a valuable coproduct.

13 Claims, 1 Drawing Figure

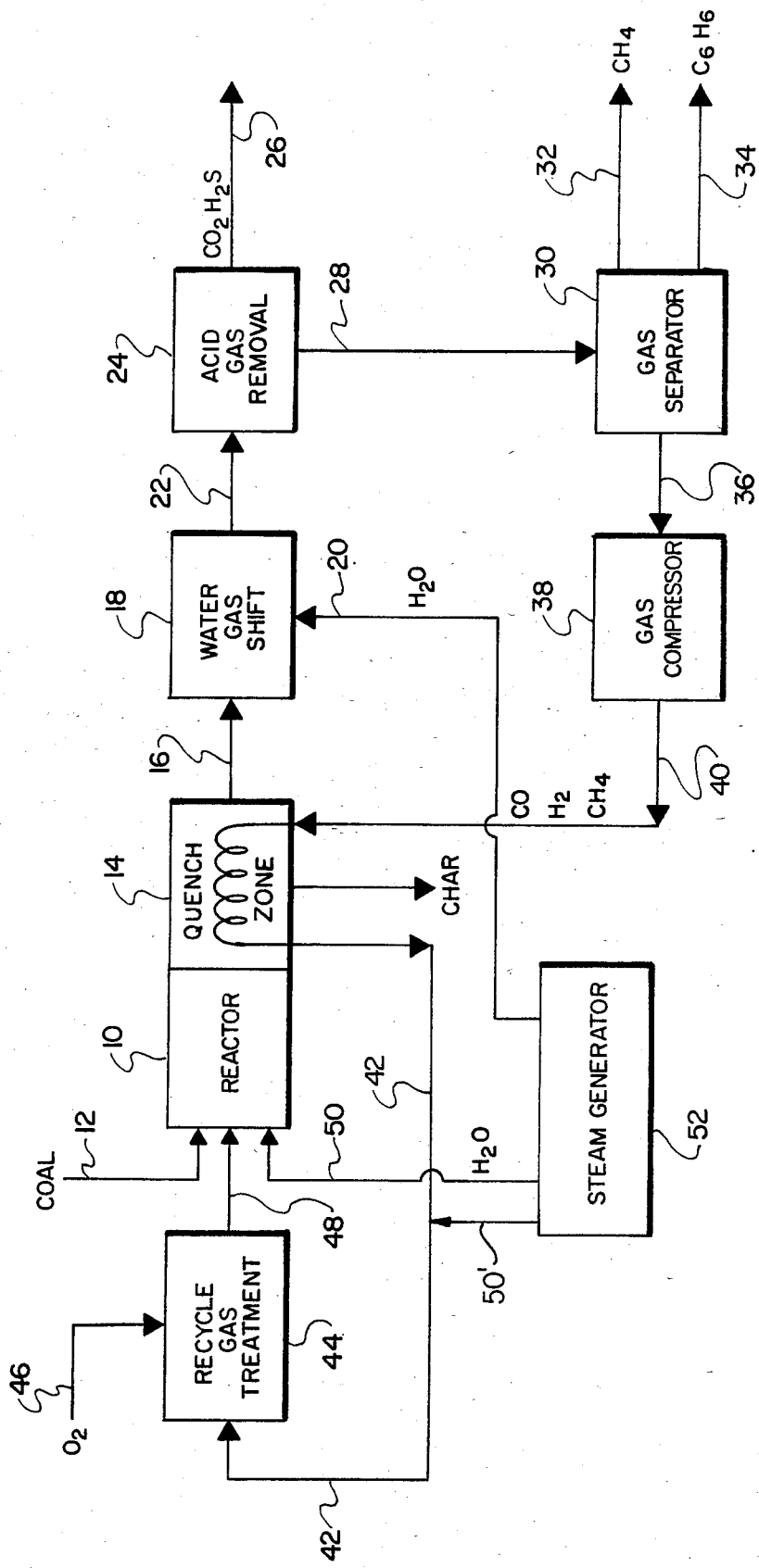

HYDROPYROLYSIS PROCESS

STATEMENT OF GOVERNMENT INTEREST

The Government has rights in this invention pursuant to Contract (or Grant) No. DE-AT21-78ET10328 awarded by the U.S. Department of Energy.

This is a continuation of co-pending application Ser. No. 06/432,231 filed on Oct. 1, 1982, now abandoned.

BACKGROUND OF THE INVENTION

The present invention relates to a process for preparing a high-Btu content gas by the reaction of a hydrogen-containing pyrolysis gas with a hydrogen-deficient carbonaceous material at an elevated temperature and pressure. It particularly relates to such a process wherein the pyrolysis gas comprises hydrogen as the principal constituent and the balance consists essentially of carbon monoxide, steam and methane such that substantially no additional external source of hydrogen is required for the process.

It has been known for hundreds of years that a combustible gas could be produced from coal by simply heating the coal in a closed vessel. It was not until the 1800's, however, that a manufactured gas industry began. In the latter part of the 1800's, the water-gas process was developed in which steam was reacted with hot coal to produce large quantities of a combustible gas. The combustible gas produced by the water-gas process had to be enriched by carburetting it (adding volatile hydrocarbons) to increase its Btu content to a level at which it was suitable for illumination applications. This technology was inefficient by today's standards. Nonetheless, it accounted for over half of the manufactured gas production in the United States as late as the middle 1900's. Manufactured gas was gradually replaced by natural gas as new reserves were developed and pipelines constructed for its distribution.

In recent years worldwide concern has arisen over the rapid increase in petroleum and natural gas consumption, and the realization that the world's supplies of petroleum and natural gas are limited. Accordingly, considerable effort is being expended to develop alternate sources of energy. One such alternate energy source is synthetic petroleum and synthetic (or substitute) natural gas (SNG) produced by the conversion of coal. The advantages of converting coal to a substitute natural gas (essentially methane) are that the United States has enormous established reserves of coal that can readily be mined, the distribution and end use apparatus for the gas are presently in existence and SNG is a relatively clean burning fuel.

Several coal gasifier systems have been demonstrated on a commercial scale. The most widely known of these is the Lurgi system which is in commercial operation in South Africa. Also in use are the Winkler and Koppers-Totzek systems. All of these systems gasify coal with a mixture of steam and oxygen. A disadvantage of these systems is that a substantial amount of the coal is consumed in generating the heat required for the steam to react with the coal. In addition, the temperatures required for a rapid reaction and significant conversion of the coal are relatively high and do not favor methane formation. Thus, the gaseous products produced must be further processed if the desired product is methane.

It also has been proposed to react coal with hydrogen at elevated temperatures to produce a substantially high yield of methane directly. This approach, however, requires a separate reactor for the production of the large amounts of hydrogen consumed in the process, which adds considerably to the complexity of the process and the expense of the methane produced. Thus, various processes have been proposed to obviate some of these disadvantages and provide a means for the production of methane from coal which is both economical and energy efficient.

U.S. Pat. No. 4,162,959 describes a process for the production of hydrogenated hydrocarbons. A solid carbonaceous material is pyrolyzed in the presence of a particulate source of heat to yield a particulate carbon-containing residue and volatilized hydrocarbons, while simultaneously the volatilized hydrocarbons are hydrogenated. The particulate source of heat is formed by oxidizing carbon in the solid residue to heat the particles. Hydrogen for the process is obtained by reacting at least a portion of the hot particulate carbon-containing residue of pyrolysis with steam prior to feeding the particulate residue to the pyrolysis reaction zone. Thus, this process utilizes three reaction zones; namely, an oxidation zone, a hydrogen generation (conversion) zone, and a pyrolysis zone.

U.S. Pat. No. 4,183,733 describes a hydro gas plant comprising the combination of a gasifier into which raw coal is introduced for hydrogasification that results in the production of methane; a furnace for cracking the methane into hydrogen and carbon monoxide; and means for utilizing the combustion heat of the residual coke obtained during the operation of the gasifier. Thus this process obtains its hydrogen for hydrogasification by cracking a portion of the methane product.

U.S. Pat. No. 4,217,201 describes an integrated coal cleaning, liquefaction and gasification process. In the disclosed process, coal is finely ground and cleaned so as to preferentially remove denser ash-containing particles along with some coal. The resulting clean coal portion having a reduced ash content is then fed to a coal hydrogenation system for the production of desirable hydrocarbon gases and liquid products. The remaining ash-enriched coal portion is gasified in a separate reactor to produce a synthesis gas which is then shift converted with steam and purified to produce high purity hydrogen for the coal hydrogenation system. Thus this process requires two separate reactors—one for hydrogenation and another to produce a synthesis gas for conversion to hydrogen for use in the process.

Another process for the production of substitute natural gas from coal utilizing catalytic gasification is described by J. E. Gallagher, Jr. and H. A. Marshall of Exxon Research and Engineering Company in "Production of SNG from Illinois Coal Via Catalytic Gasification," *A.I.Ch.E. Symposium on Reaction Engineering in Processing Solid Fossil Fuels*, November 1978, Miami Beach, Fla. In the disclosed process, dried coal is coated with potassium hydroxide catalyst. The coated coal is then reacted in a fluidized bed with a preheated mixture of steam, recycle hydrogen and carbon monoxide to produce a product gas substantially free of any heavy hydrocarbons. Any acid gases present in the product gas are removed, and the remaining gas, consisting essentially of only hydrogen, carbon monoxide and methane, is sent to a cryogenic distillation system. The methane is separated, and the CO and $H_2$ are mixed with gasification steam and recycled to the gasifier. In the presence of the catalyst, the carbon monoxide and hydrogen react to produce methane and generate heat in a sufficient quantity to substantially offset the concurrent endothermic reaction between the steam and coal. The principal disadvantage of this process is that it requires a catalyst and a separate catalyst recovery system.

In spite of the intensive research being done in the area of coal gasification there still exists a need for further improvement in processes for the gasification of coal to produce methane.

SUMMARY OF THE INVENTION

The present invention provides an improvement in a process wherein a hydrogen-deficient carbonaceous material is treated in a reaction zone with a hydrogen-containing pyrolysis gas at an elevated temperature and pressure to produce a product gas mixture including methane, carbon monoxide and hydrogen. In accordance with the present invention, the requirement for an external source of hydrogen for use in such a process is eliminated, although one may be used if desirable. The improvement comprises introducing the product gas mixture into a water-gas shift reaction zone where it is contacted with a controlled amount of steam to react with at least a part of the carbon monoxide to produce additional hydrogen. The gas mixture containing additional hydrogen is withdrawn from the water-gas shift reaction zone and introduced into a gas separation zone. Generally, the gas separation zone will include means for removal of acid gases and further includes a cryogenic separation zone to separate the remaining gas mixture into its constituent parts and produce a product gas comprising methane, and a recycle gas comprising hydrogen, carbon monoxide and methane for use in the process.

A controlled amount of steam is also provided for use in the process. The steam is combined with the hydrogen, carbon monoxide and methane which were separated for recycle. This combined gas mixture is used as the hydrogen-containing pyrolysis gas for treatment of additional hydrogen-deficient carbonaceous material. The composition of the pyrolysis gas is adjusted by controlling the amount of steam added and the conditions in the water-gas shift reaction zone and gas separation zone to provide a pyrolysis gas comprising hydrogen as a principal constituent and further including a minor amount of carbon monoxide, steam and methane such that no external source of hydrogen is required for the process.

In accordance with a particularly preferred embodiment of the invention, in addition to the methane product there also is produced benzene as a valuable coproduct. Specifically, the pyrolysis gas and hydrogen-deficient carbonaceous material are reacted in the reaction zone at a temperature of from 760° to 1260° C. (1400° to 2300° F.) at a pressure of from about 3.5 to 10.5 megapascals (500 to 1500 psia) for a time of from about 0.5 to 15 seconds, whereby the product gas mixture also includes significant quantities of benzene in addition to methane.

The present invention provides many advantages over the prior art processes. For example, hydrogen required for the process is produced by controlling the composition of the pyrolysis gas such that a separate source of hydrogen is not required. Thus, the requirements for a separate hydrogen generator and the associated equipment to produce hydrogen for introduction into the system along with the expense and maintenance problems associated therewith are not incurred. Still further, any unreacted or partially reacted hydrogen-deficient carbonaceous material (e.g., char) is readily recoverable and provides a source of fuel for producing steam or electricity for use in the process, or alternatively represents a saleable product, thus, enhancing the economics of the process. These and other features, aspects and advantages of the present invention will become better understood with reference to the following description, appended claims and the accompanying drawing.

BRIEF DESCRIPTION OF THE DRAWING

The sole FIGURE shows a schematic of a process embodying the features of the present invention.

DETAILED DESCRIPTION OF THE INVENTION

The present invention relates to an improvement in a process wherein a hydrogen-deficient carbonaceous material is treated in a reaction zone with a hydrogen-containing pyrolysis gas at an elevated temperature and pressure to produce, among other things, a methane product. Broadly, the term "hydrogen-deficient carbonaceous material" refers to any carbon- and hydrogen-containing material in which the carbon-to-hydrogen mole ratio is less than that of the desired methane product, such that the addition of hydrogen is required to convert any substantial quantity of the material to methane. It particularly relates, however, to those carbonaceous materials which are available in abundance and at relatively low cost so that they may be economically utilized as feedstocks for producing methane.

The process of the present invention is particularly applicable for use with those hydrogen-deficient carbonaceous materials wherein the carbon-to-hydrogen ratio is greater than 0.5. Typical of such materials are the various coals and coal-like substances such as anthracite coal and bituminous coal, subbituminous coal, lignite, peat, oil shale, tar sands and kerogen. The process of the present invention can also utilize other materials such as petroleum products and byproducts, biomass, organic chemical waste and carbon-rich municipal waste.

In accordance with the present invention, there is provided a reactor 10 which defines a reaction zone into which is introduced a hydrogen-deficient carbonaceous material, such as, for example, a stream 12 of coal. Generally, a carrier gas is used to convey the hydrogen-deficient carbonaceous material. The selection of the carrier gas is not particularly critical, provided of course it does not interfere with formation of the desired reaction products. Specifically, the carrier or transport gas for the hydrogen-deficient carbonaceous material should not include any substantial amounts of free or elemental oxygen. Thus, gases such as nitrogen or steam may be utilized or the gaseous reaction products themselves of this process may be used. A particularly preferred carrier gas is hydrogen or a hydrogen-enriched gas.

In reactor 10 the hydrogen-deficient carbonaceous material is reacted with a hydrogen-containing pyrolysis gas. A key feature of the present invention is the composition of the pyrolysis gas in which hydrogen is the principal constituent. Illustratively, the pyrolysis gas will consist essentially of 40–90 vol. % hydrogen, 6–30 vol. % steam, 1 to 10 vol. % carbon monoxide and 3 to 20 vol. % methane, based on the total volume of the pyrolysis gas. Generally, the amounts of carbon monoxide, steam and methane are controlled such that hydrogen comprises at least 50 vol. % of the pyrolysis gas.

Particularly good results are obtained with coal, a preferred carbonaceous material, when the pyrolysis gas is introduced into reactor 10 in an amount to provide a mole ratio of hydrogen to carbon within the range of from about 1:1 to 5:1 and a mole ratio of steam to carbon within the range of from about 0.1:1 to 2:1.

The process of the present invention may be utilized with substantially any type of solids-gas reactor such as a fluidized bed reactor, a fixed bed reactor or an entrained flow reactor. The particularly preferred reactors are fluidized bed reactors and entrained flow reactors such as the entrained flow reactor described in U.S. Pat. No. 4,323,538. In reactor 10 (an entrained flow reactor) the hydrogen-deficient carbonaceous material undergoes, among other things, pyrolysis to form char and volatilized hydrocarbons. The term "char" refers to the combustible carbonaceous residue remaining after pyrolytic treatment of the carbonaceous material, for example, coal. In addition, a portion of the carbon content of the carbonaceous material is steam gasified in the reactor to produce carbon monoxide and hydrogen. The other principal reactions taking place are the hydrogenation and pyrolysis of the carbonaceous material to produce methane, and, under particularly preferred conditions, significant quantities of benzene. Additional reactions which can occur include steam reforming of methane or other hydrocarbons and methanation of carbon monoxide.

The residence time of the carbonaceous material in reactor 10 will vary depending upon the type of reactor that is utilized. In order to obtain a high yield of methane and significant quantities of valuable coproducts such as benzene, using an entrained flow reactor, the residence time of the carbonaceous material generally will be within the range of about 1 to 15 seconds and preferably from about 2 to 10 seconds. As used herein the term "residence time" refers to the average time that the carbonaceous material is maintained within the desired reaction temperature range.

The temperature maintained in the reaction zone may vary depending upon such parameters as the temperature of the pyrolysis gas introduced into reactor 10, the temperature of the carbonaceous material introduced into reactor 10, and the composition of the pyrolysis gas, which will influence the reactions taking place, i.e., endothermic and exothermic reactions. Generally, it is preferred to maintain the temperature in the reactor within the range of from about 649° to 1371° C. (1200° to 2500° F.), preferably from about 760° to 1260° C. (1400° to 2300° F.). Specifically, at higher temperatures substantially little valuable coproducts such as benzene are formed, whereas at lower temperatures the reaction rates are too slow to obtain significant quantities of the desired products or substantial conversion of the carbonaceous material. In addition, it will be appreciated that at the shorter residence time the higher temperature range is preferred, while at the longer residence times, the lower temperature range is utilizable. The pressure in reactor 10 generally is maintained within the range of from about 0.7 to 21 megapascals (MPa) (100 to 3000 psia) and preferably 3.5 to 10.5 megapascals (500 to 1500 psia).

An effluent gas from reactor 10 passes into a quench zone 14 where it is preferably passed in indirect heat-exchange relationship with a cooling fluid. Advantageously, the char also is removed for use as a source of fuel for generating steam or producing electricity for the process, or as a saleable product. While in the preferred embodiment depicted, quench zone 14 comprises an indirect heat exchanger, it will be readily apparent that it also could be a direct cooler in which the reaction products are contacted with a cooling fluid such as water or recycled product gases.

A stream 16 of the quenched reactor effluent gas principally comprising methane, carbon monoxide, hydrogen and steam, and optionally containing benzene, is next introduced into a water-gas shift reactor 18 where it is contacted with a stream 20 of a controlled amount of steam which reacts with at least a part of the carbon monoxide to form additional hydrogen and carbon dioxide. A mixed gas stream 22 of increased hydrogen content is withdrawn from water-gas shift reactor 18 and introduced into an acid gas removal system 24. In acid gas removal system 24 there is produced an acid gas stream 26 principally comprising $CO_2$ and $H_2S$ and a product gas stream 28 principally comprising hydrogen, methane, carbon monoxide and benzene.

Stream 28 is introduced into a gas separator 30 which typically will be a cryogenic separator. In gas separator 30 there is produced under controlled conditions a product methane stream 32 and a coproduct benzene stream 34. There also is produced a recycle gas stream 36 which will consist essentially of hydrogen, carbon monoxide and methane which is introduced into a gas compressor 38 to produce a compressed recycle gas stream 40. The compressed recycle gas stream then passes through quench zone 14 wherein it extracts heat from the reaction products from reactor 10 to produce a heated recycle gas stream 42. Gas stream 42 is then introduced into a recycle gas treatment zone 44. The principal purpose of the recycle gas treatment zone is to increase the gas temperature to a sufficient level to maintain a desired temperature range within reactor 10. Also introduced into recycle gas treatment zone 44 is a source of oxygen 46 which is reacted with a portion of the recycle gas stream to produce heat. The oxygen 46 reacts principally with hydrogen to generate additional steam, and to a lesser extent with methane and carbon monoxide to form additional carbon monoxide and carbon dioxide.

A subdivided recycle gas stream may be formed in the gas separator 30 into hydrogen-rich and -deficient portions. These portions may be mixed independently with portions of the oxygen 46 in the recycle gas treatment zone 44 so as to control the relative quantities of hydrogen, methane and carbon monoxide reacting with said oxygen.

A treated gas stream 48 from recycle gas treatment zone 44 is introduced into reactor 10. Also introduced into reactor 10 is a stream 50 of steam from a steam generator 52. The two gas streams 48 and 50 together comprise the pyrolysis gas for the treatment of additional hydrogen-deficient carbonaceous material. It will be appreciated that it is possible and may be preferred to combine streams 42 and 50 via stream 50' and introduce the combined streams into treatment zone 44.

The essence of the present invention is the means by which the operation of reactor 10 and the downstream processing loops described above are controlled, so that the amount and composition of pyrolysis gas which reacts with the carbonaceous material in reactor 10 is such that the need for an external make-up hydrogen stream is eliminated. If this amount and composition of pyrolysis gas does not exist initially, the present invention provides the steps to be taken to cause operation of the system to approach the desired condition immediately or progressively. Specifically, during the course of the reactions occurring in reactor 10 the composition of the pyrolysis gas generally will become enriched or depleted in each of the four pyrolysis gas components (hydrogen, steam, carbon monoxide and methane). The object of the product gas processing control is to adjust the composition and flow rate of the product gas stream to the conditions existing at the reactor entrance without the necessity of introducing an external make-up stream of hydrogen or of any of the other pyrolysis gas constituents with the exception of steam.

Hydrogen and steam are the primary reactants with the carbonaceous material such as coal or coal-derived volatiles, being able to gasify these materials either by hydropyrolysis or steam gasification, respectively. The balance between hydrogen and steam in the pyrolysis gas can therefore be used to influence the relative amounts of hydrocarbon products (e.g., methane) formed from hydrogen reactions, and carbon oxides (e.g., carbon monoxide) produced from steam gasification and reforming reactions. Since the production of hydrocarbons consumes hydrogen, while steam gasification and reforming reactions produce hydrogen directly or through downstream processing, the net hydrogen consumption can be adjusted in this manner. The adjustment is made such that the net hydrogen consumption is zero. In general, a higher hydrogen concentration or lower steam concentration will serve to increase net hydrogen consumption, while the reverse decreases net hydrogen consumption. The quantity of hydrogen in the pyrolysis gas can be adjusted progressively by varying the conversion of carbon monoxide in the water-gas shift reactor, while the quantity of steam is adjusted directly by controlling the rate at which it is injected into reactor 10.

The methane and carbon monoxide compositions can be used in a similar fashion to direct the process toward a zero net hydrogen consumption. Methane will tend to inhibit hydrogenation reactions which yield methane or other hydrocarbons. In addition to suppressing methane production, higher concentrations of methane (or steam) enhance the rate of steam reforming, thereby increasing the production of hydrogen and carbon monoxide in the reactor. Thus, the methane concentration can be used to adjust the net hydrogen production, with higher methane concentrations generally favoring increased hydrogen production and lower concentrations favoring increased hydrogen consumption. In an analagous way, carbon monoxide generally suppresses the steam reforming and gasification reactions. Therefore higher carbon monoxide concentrations favor increased hydrogen consumption, while lower concentrations favor higher hydrogen production rates.

Additional reaction parameters which may be controlled to further the purposes of the present invention include temperature, pressure and residence time. These parameters can also be adjusted to obtain the desired net hydrogen production rate and to achieve a pyrolysis gas composition which is restored when gaseous products are processed as described above. High pressure generally favors methane formation compared to steam reforming and gasification reactions. Thus, increasing the pressure generally increases the net hydrogen consumption, while lower pressure generally decreases net hydrogen production. The steam gasification and reforming reactions are generally favored over hydropyrolysis by higher temperatures, so that increased temperature can be used to increase hydrogen production while decreased temperature has the opposite effect. Longer reaction times generally favor at least the steam gasification reaction, thus increasing the hydrogen production.

While these characterizations may depend on the nature of the carbonaceous feedstock and the reactor process conditions, in each case some such trend will exist such that a particular direction of change of a particular parameter increases or decreases the net hydrogen production or consumption. Judicious changes or combinations of changes in the pyrolysis gas composition for any given set of reactor operating conditions can therefore be developed from the procedures outlined above which will direct the process to a zero net consumption of hydrogen or to some equivalent desired condition at which substantially no external source of make-up hydrogen is required.

The following example illustrates the advantages to be obtained by the practice of the present invention but should not be construed as a limitation on the scope of the invention.

EXAMPLE

This example is based on the use of the entrained flow reactor described in U.S. Pat. No. 4,323,538. Stream numbers used correspond to those in the sole figure of the present drawing. The flows are scaled to produce 263.5 terajoules ($250 \times 10^9$ Btu) per day of substitute natural gas (SNG) from Kentucky No. 9 high-volatile A-bituminous (hvAb) coal.

Recycle gas stream 36 is pressurized and preheated to 816° C. (1500° F.) and 7.6 megapascals (MPa) (1100 psia) by passage through gas compressor 38 and quench zone 14, thereby effecting a partial recovery of heat from the reacting material. The resulting preheated recycle gas stream 42, having a molar composition of 69.3% hydrogen, 8.4% carbon monoxide, 11.1% methane, and 11.2% steam and a flow rate of 147,670 kg-mol/hr (325,560 lb-mol/hr), is further heated in the recycle gas treatment zone 44 by combustion with 149.3 metric tons/hr (164.5 short tons/hr) of oxygen of 99.5 wt. % purity fed at 149° C. (300° F.) and 8.3 MPa (1200 psia). In the recycle gas treatment zone 44, essentially all of the oxygen reacts with hydrogen to form additional steam. The resultant treated gas stream 48, which comprises hydrogen, carbon monoxide, methane and steam at a temperature of 1032° C. (1890° F.) and pressure of 7.6 MPa (1100 psia), is fed to reactor 10.

Sufficient Kentucky No. 9 hvAb coal is ground to 70% minus 200-mesh and dried to 2 wt. % moisture to give a coal feed stream 12 of 898,230 kg/hr (1,980,230 lb/hr) of coal on a moisture-free basis. This stream is fed through a series of lock hoppers to reactor 10 in dense-phase flow, at a temperature of approximately 93° C. (200° F.) and a pressure of 6.9 MPa (1000 psia). In reactor 10 the coal is mixed rapidly and heated with treated gas stream 48.

Following mixing of the pyrolysis gas and coal in reactor 10, reaction is allowed to proceed for 2.4 seconds. At the end of this time, the temperature is 978° F.) and the pressure has dropped by approximately 100 kPa (15 psi). An effluent gas from reactor 10 is cooled in the quench zone 14 to approximately ambient temperature, and leaves with some water, benzene, and soluble materials (e.g., ammonia) condensed out. This quenched stream 16 is then further processed to recover products and to regenerate recycle gas 42.

This further processing proceeds through a series of steps which are conventional and readily available technology. The effluent gas stream 16 is mixed with a controlled quantity of steam 20 and reacted in the water-gas shift reactor 18 until the flow rate of carbon monoxide in mixed gas stream 22 equals that present in heated recycle gas stream 42, 102,420 kg-mol/hr (27,325 lb-mol/hr). If the operating conditions in the reactor zone 10 have been chosen correctly, the hydrogen flow rate in mixed gas stream 22 will also be restored to that in heated recycle gas stream 42, 102,420 kg-mol/hr (225,800 lb-mol/hr). The method by which the gas composition is controlled, as described hereinbefore, comprises the essence of the present invention.

Mixed gas stream 22 is then cooled and partially dried, and sent to acid gas removal zone 24. There, acid gases, including carbon dioxide, hydrogen sulfide and carbonyl sulfide are removed in stream 26. A product gas stream 28 is dried and sent to gas separator 30. Product gas stream 28 is separated by cryogenic distillation into a product methane stream 32 and a coproduct benzene stream 34. After appropriate treatment and purification, stream 34 yields 2390 cubic meters/day (15,030 bbl/day) of chemical-grade benzene. In performing this cryogenic separation in gas separator 30, sufficient methane is removed so that the flow rate of methane in recycle gas stream 36 is the same as that initially in heated recycle gas stream 42, 16,490 kg-mol/hr (36,350 lb-mol/hr). Recycle gas stream 36 is then compressed and mixed with sufficient steam (16,599 kg-mol/hr [36,490 lb-mol/hr]) to restore the composition and total flow rate of heated recycle gas stream 42.

The preceding representative Example may be varied within the scope of the present invention as will be readily understood by those skilled in the art. Thus, the foregoing detailed description has been given for completeness of understanding only and no unnecessary limitations are to be implied therefrom. Accordingly, while the invention has been described as being practiced in the absence of an added catalyst there may be instances wherein it may be desirable to add a catalyst to enhance the rate of desired reactions or the yield of the desired methane product and coproducts such as benzene or light aliphatic hydrocarbons. In addition, while the invention has been described with respect to an entrained flow reactor, there will be instances when it will be preferred to practice the invention utilizing, for example, a fluidized bed reactor. In such instance, the residence time in the reactor of the hydrogen-deficient carbonaceous material will be substantially greater than described in the preceding Example. Such increased residence time provides the advantage of obtaining a substantial increase in the conversion of the carbonaceous material to desired products.

It will of course be realized that various other modifications can be made in the design and operation of the present invention without departing from the spirit thereof. Thus, while the principle, preferred construction, and mode of operation of the invention have been explained and what is now considered to represent its best embodiment has been illustrated and described, it should be understood that within the scope of the appended claims the invention may be practiced otherwise than as specifically illustrated and described.

What is claimed is:

1. A process for producing methan by reacting a hydrogen-deficient carbonaceous material with a hydrogen-containing pyrolysis gas having a composition selected and controlled so that no external source of hydrogen is needed to provide the hydrogen requirements for the overall process, which comprises the sequential steps of:
   (a) introducing said pyrolysis gas at an elevated temperature and pressure and said carbonaceous material into a single pyrolysis zone of an entrained flow reactor (10) to react to form a product gas mixture including methane, carbon monoxide and a reduced content of hydrogen relative to that in said pyrolysis gas;
   (b) reacting a part of the carbon monoxide in said product gas mixture with a first controlled amount of steam in a water-gas shift reaction zone (18) sufficient to produce hydrogen in an amount substantially equal to the hydrogen consumed in the overall process;
   (c) withdrawing from said water-gas shift reaction zone a shifted gas mixture containing additional hydrogen and introducing said shifted gas mixture into a gas separation zone (30);
   (d) separating the shifted gas mixture in said gas separation zone into (1) a product comprising methane, and (2) a recycle gas comprising hydrogen, carbon monoxide and methan;
   (e) introducing said recycle gas from step (d) (2), a controlled amount of an oxygen-containing gas and a second controlled amount of steam into a gas treatment zone (44) for partial oxidation of the recycle gas to produce said pyrolysis gas having said elevated temperature for introduction into said entrained flow reactor (10); and
   (f) controlling steps (b), (d) and (e) to obtain, under steady-state conditions, a composition of the pyrolysis gas wherein hydrogen is the principal constituent and the remainder consists essentially of a monor amount each of carbon monoxide, steam and methane so that no external source of hydrogen is needed to provide the hydrogen requirements for the overall process.

2. The process of claim 1 wherein the step (f) the composition of the pyrolysis gas is controlled to comprise from about 1 to 10% carbon monoxide, 3 to 20% methane, 60 to 30% steam, and 40 to 90% hydrogen.

3. The process of claim 2 wherein said elevated temperature in said reactor is maintained within the range of from about 649° C. to 1371° C.

4. The process of claim 3 wherein the pressure in said reactor is maintained within the range of from about 0.7 to 21 megapascals.

5. The process of claim 4 wherein said hydrogen-deficient carbonaceous material and pyrolysis gas are maintained at said elevated temperature in said reactor for a residence time within the range of from about 1 to 15 seconds.

6. The process of claim 5 wherein said hydrogen-deficient carbonaceous material has a carbon to hydrogen mole ratio greater than 0.5.

7. The process of claim 2 wherein the mole ratio of the hydrogen present in said pyrolysis gas to the carbon content of said hydrogen-deficient carbonaceous material is within the range of about 1:1 to 5:1.

8. The process of claim 7 wherein the mole ratio of steam present in said pyrolysis gas to the carbon content of said hydrogen-deficient carbonaceous material is within the range of from about 0.1:1 to 2:1.

9. A process for producing methane and benezene by reacting a hydrogen-deficient carbonaceous material with a hydrogen-containing pyrolysis gas having a composition selected and controlled so that no external source of hydrogen is needed to provide the hydrogen requirements for the overall process, which comprises the sequential steps of:

(a) introducing said pyrolysis gas consisting essentially of from about 1 to 10% carbon monoxide, 3 to 20% methane, 6 to 30% steam and a balance of hydrogen, at an elevated temperature and pressure, and said carbonaceous material into a single pyrolysis zone of an entrained flow reactor (10) to react said hydrogen-deficient carbonaceous material with said pyrolysis gas at a temperature within the range of from about 760° C. to 1260° C., at a pressure of from about 3.5 to 10.5 megapascals and for a time of from about 2 to 10 seconds, to form a product gas mixture including methane, benzene, carbon monoxide and a reduced hydrogen content relative to that in said pyrolysis gas;

(b) reacting a part of the carbon monoxide in said product gas mixture with a first controlled amount of steam in a water-gas shift reaction zone (18) sufficient to produce hydrogen in an amount substantially equal to the hydrogen consumed in the overall process;

(c) withdrawing from said water-gas shift reaction zone a shifted gas mixture contaiing additional hydrogen and introducing said shifted gas mixture into a gas separation zone (30);

(d) separating the shifted gas mixture in said gas separation zone into (1) a product comprising methane and benzene, and (2) a recycle gas comprising hydrogen, carbon monoxide and methane;

(e) introducing said recycle gas from step (d)(2), a controlled amount of an oxygen-containing gas and a second controlled amount of steam into a gas treatment zone (44) for partial oxidation of the recycle gas to produce said pyrolysis gas having said elevated temperature for introduction into said entrained flow reactor (10); and (f) controlling steps (b), (d) and (e) to obtain, under steady-state conditions, a composition of the pyrolysis gas mixture of step (a) so that no external source of hydrogen is needed to provide the hydrogen requirements for the overall process.

10. The process of claim 9 wherein said hydrogen-deficient carbonaceous material is coal.

11. The process of claim 10 wherein the mole ratio of the hydrogen present in said pyrolysis gas to the carbon content in said coal is within the range of from about 1:1 to 5:1.

12. The process of claim 11 wherein the mole ratio of the steam present in said pyrolysis gas to the carbon content in said coal is within the range of from about 0.1:1 to 2:1.

13. The process of claim 9 wherein in step (b) the resulting product gas mixture further includes entrained unreacted and partially reacted hydrogen-deficient carbonaceous material which is recovered and used as a source of fuel to provide heat for producing steam for steps (d) and (g).

* * * * *